United States Patent
Lee et al.

(10) Patent No.: US 12,180,443 B2
(45) Date of Patent: Dec. 31, 2024

(54) APPARATUS FOR PRODUCING FERMENTED SOYBEAN MEAL

(71) Applicant: FEEDUP CO., LTD., Nonsan-si (KR)

(72) Inventors: Jong Hwa Lee, Sejong (KR); Hyuck Gee Lee, Icheon-si (KR); Sung Min Lee, Suwon-si (KR); Hee Sung Lee, Ansan-si (KR)

(73) Assignee: FEEDUP CO., LTD., Nonsan-si (KR)

( * ) Notice: Subject to any disclaimer, the term of this patent is extended or adjusted under 35 U.S.C. 154(b) by 681 days.

(21) Appl. No.: 17/275,791

(22) PCT Filed: Jan. 31, 2019

(86) PCT No.: PCT/KR2019/001390
§ 371 (c)(1),
(2) Date: Mar. 12, 2021

(87) PCT Pub. No.: WO2020/122317
PCT Pub. Date: Jun. 18, 2020

(65) Prior Publication Data
US 2022/0049200 A1     Feb. 17, 2022

(30) Foreign Application Priority Data

Dec. 10, 2018  (KR) .................. 10-2018-0158389

(51) Int. Cl.
*C12M 1/16*  (2006.01)
*A23K 10/12*  (2016.01)
(Continued)

(52) U.S. Cl.
CPC ............ *C12M 21/16* (2013.01); *A23K 10/12* (2016.05); *A23K 10/30* (2016.05); *A23K 30/20* (2016.05);
(Continued)

(58) Field of Classification Search
None
See application file for complete search history.

(56) References Cited

U.S. PATENT DOCUMENTS

| 4,870,022 A | * | 9/1989 | Fukuyasu | .............. A23L 11/50 99/275 |
| 2011/0287477 A1 | * | 11/2011 | Tang | ...................... A23J 3/346 435/68.1 |

(Continued)

FOREIGN PATENT DOCUMENTS

| CN | 203124392 | | 8/2013 |
| CN | 105410554 | * | 3/2016 |

(Continued)

OTHER PUBLICATIONS

Tomé ("Lysine Requirement through the Human Life Cycle"). 2007. (Year: 2007).*

(Continued)

*Primary Examiner* — Holly Kipouros
*Assistant Examiner* — Nathan G Esperon
(74) *Attorney, Agent, or Firm* — LEX IP MEISTER, PLLC

(57) ABSTRACT

An exemplary embodiment of the present invention provides an apparatus for producing fermented soybean meal, which produces fermented soybean meal for monogastric animals and ruminants selectively or together. An apparatus for producing fermented soybean meal according to an exemplary embodiment of the present invention includes: a solid-liquid separating part, which mixes raw material soybean meal and an extraction solvent and extracts the soybean meal, and separately produces a remaining soybean meal and a soybean meal extract; a lactic acid bacteria culturing part, which produces the lactic acid bacteria by putting inoculum into the soybean meal extract, and supplies the lactic acid bacteria to the solid-liquid separating part; a solid substrate (Continued)

fermenting part, which is selectively supplied with and mixes at least two of the remaining soybean meal supplied from the solid-liquid separating part, the raw material soybean meal supplied through bypass, and lactic acid bacteria supplied from the lactic acid bacteria culturing part to produce a mixed material, and solid-substrate ferments the mixed material to produce primary solid substrate fermented soybean meal; and a drier, which dries the primary solid substrate fermented soybean meal supplied from the solid substrate fermenting part to produce secondary solid substrate fermented soybean meal.

14 Claims, 11 Drawing Sheets

(51) Int. Cl.
| | |
|---|---|
| *A23K 10/30* | (2016.01) |
| *A23K 30/20* | (2016.01) |
| *A23K 40/10* | (2016.01) |
| *A23K 50/10* | (2016.01) |
| *A23N 17/00* | (2006.01) |
| *B01D 21/26* | (2006.01) |
| *B04B 5/10* | (2006.01) |
| *C12M 1/00* | (2006.01) |
| *C12M 1/02* | (2006.01) |

(52) U.S. Cl.
CPC .............. *A23K 40/10* (2016.05); *A23K 50/10* (2016.05); *A23N 17/007* (2013.01); *B01D 21/262* (2013.01); *B04B 5/10* (2013.01); *C12M 23/20* (2013.01); *C12M 27/00* (2013.01); *C12M 29/06* (2013.01); *C12M 29/18* (2013.01); *C12M 47/14* (2013.01)

(56) References Cited

U.S. PATENT DOCUMENTS

| | | | | |
|---|---|---|---|---|
| 2014/0284501 | A1* | 9/2014 | Medoff | B01D 61/44 |
| | | | | 250/492.3 |
| 2016/0015055 | A1* | 1/2016 | Kang | A23K 50/10 |
| | | | | 426/46 |
| 2020/0339932 | A1* | 10/2020 | Farmer | C12M 21/16 |

FOREIGN PATENT DOCUMENTS

| | | | |
|---|---|---|---|
| CN | 206213206 | * | 6/2017 |
| CN | 107385003 | | 11/2017 |
| CN | 107535699 | | 1/2018 |
| CN | 107904094 | * | 4/2018 |
| CN | 208104363 | * | 11/2018 |
| JP | H0430756 | * | 2/1992 |
| JP | H09289890 | * | 11/1997 |
| JP | 2008-126187 | | 6/2008 |
| KR | 20-1996-0014526 | | 5/1996 |
| KR | 10-2009-0109223 | | 10/2009 |
| KR | 20110067267 | * | 6/2011 |
| KR | 10-1216669 | | 12/2012 |
| KR | 20-0466922 | * | 5/2013 |
| KR | 10-2013-0107866 | | 10/2013 |
| KR | 10-2014-0144585 | | 12/2014 |
| KR | 10-1467250 | | 12/2014 |
| KR | 20140144585 | * | 12/2014 |
| KR | 10-1485554 | | 1/2015 |
| KR | 10-2016-0130950 | | 11/2016 |
| KR | 20160143114 | * | 12/2016 |
| KR | 10-1786386 | | 10/2017 |
| WO | WO-2011091999 A1 | * | 8/2011 ............. A01K 39/01 |

OTHER PUBLICATIONS

KIPO, PCT Search Report & Written Opinion of PCT/KR2019/001390 dated Sep. 10, 2019.
Li Jian "Research and Development Progress of Fermented Soybean Meal" Cereal and Feed Industry 2009.6 (2009) pp. 31-35.
Cai Jiancheng et al., "Composting Engineering and Composting Plant", Hubei Provincial Institute of Mechanical and Electrical Engineering, Mechanical Industry Press, Feb. 27, 2024, 6 pages.

* cited by examiner

APPARATUS FOR PRODUCING FERMENTED SOYBEAN MEAL

TECHNICAL FIELD

The present invention relates to an apparatus for producing fermented soybean meal, and more particularly, to an apparatus for producing fermented soybean meal, which produces fermented soybean meal from raw material soybean meal.

BACKGROUND ART

Fermented soybean meal is a source of protein, with which fish meal is replaceable in feedstuff, and a content of crude protein acts as an important marketing point in the fermented soybean meal together with availability of amino acid.

In order to ferment soybean meal, a solid substrate fermentation method is mainly used, and an aerobic fermentation method, which mainly utilizes mold represented by aspergillus and bacteria represented by bacillus as microorganism, is a general trend.

The aerobic solid substrate fermentation method essentially requires oxygen supply, so that there are disadvantages in that a contamination possibility is high during a process, a considerable level of an investment of a facility, such as a fermentor, is required, and it is not easy to scale up a factory for increasing an output. Accordingly, the solid substrate fermentation method using anaerobic bacteria is counted as an alternative, which is capable of overcoming the disadvantages of the aerobic process.

Lactic acid bacteria that is anaerobic bacteria converts indigestible oligosaccharide that is one of the representative anti-nutritional factors of soybean meal into a beneficial substance, such as lactic acid, and makes amino acid metabolism be active, thereby being useful for livestock and producing various biologically active substances. Particularly, lactic acid secreted by lactic acid bacteria during a fermentation process may suppress the propagation of other microorganism, thereby minimizing contamination.

The solid substrate fermentation method is formed to produce fermented soybean meal for monogastric animals (for example, a pig, a chicken, and fish) having one stomach or produce fermented soybean meal for ruminant (for example, a cow) having four stomachs. The known solid substrate fermentation method cannot produce the fermented soybean meal for monogastric animals and the fermented soybean meal for ruminant selectively or together, so that there is a need for a separate facility for monogastric animals and ruminant

DISCLOSURE

Technical Problem

The present invention has been made in an effort to provide an apparatus for producing fermented soybean meal, which produces fermented soybean meal from raw material soybean meal.

The present invention has been made in an effort to provide an apparatus for producing fermented soybean meal, which produces fermented soybean meal for monogastric animals and fermented soybean meal for ruminant selectively or together.

The present invention has also been made in an effort to provide an apparatus for producing fermented soybean meal, which cultures lactic acid bacteria in large numbers in a soybean meal extract, in which carbohydrate is extracted from raw material soybean meal through an extraction process, and uses the cultured lactic acid bacteria as a starter of the fermented soybean meal.

The present invention has also been made in an effort to provide an apparatus for producing fermented soybean meal, which mass produces the residual lactic acid bacteria used as a starter into probiotics in a liquid state or after drying.

Technical Solution

An exemplary embodiment of the present invention provides an apparatus for producing fermented soybean meal, the apparatus including: a solid-liquid separating part, which mixes raw material soybean meal and an extraction solvent and extracts the soybean meal, and separately produces a remaining soybean meal and a soybean meal extract; a lactic acid bacteria culturing part, which produces the lactic acid bacteria by putting inoculum into the soybean meal extract, and supplies the lactic acid bacteria to the solid-liquid separating part; a solid substrate fermenting part, which is selectively supplied with and mixes at least two of the remaining soybean meal supplied from the solid-liquid separating part, the raw material soybean meal supplied through bypass, and lactic acid bacteria supplied from the lactic acid bacteria culturing part to produce a mixed material, and solid-substrate ferments the mixed material to produce primary solid substrate fermented soybean meal; and a drier, which dries the primary solid substrate fermented soybean meal supplied from the solid substrate fermenting part to produce secondary solid substrate fermented soybean meal.

The apparatus may further include a grinder, which grinds the secondary solid substrate fermented soybean meal supplied from the drier and finally produce tertiary solid substrate fermented soybean meal.

The solid-liquid separating part may be configured to mix supplied raw material soybean meal and an extraction solvent and immerse the soybean meal, separate remaining soybean meal and a soybean meal extract from the immersed immersion sludge, supply the separated remaining soybean meal to the solid substrate fermenting part, and supply the dehydrated soybean meal extract to the lactic acid bacteria culturing part.

The solid-liquid separating part may include any one of a centrifugal separator, a screw pressor, a filter pressor, and a decanter, which separates the remaining soybean meal and the soybean meal extract from immersion sludge.

The solid-liquid separating part may mix supplied tap water, circulating water, which circulates the lactic acid bacteria culturing part, and acidified material to produce the extraction solvent.

The lactic acid bacteria culturing part may include: a liquid fermentation tank, which injects the inoculum to the soybean meal extract supplied from the solid-liquid separating part and tap water to produce lactic acid bacteria; a lactic acid bacteria storing tank, which is connected to the liquid fermentation tank, and mixes the supplied lactic acid bacteria with tap water and stores the lactic acid bacteria; and a lactic acid bacteria service tank, which is connected to the lactic acid bacteria storing tank and supplies the supplied lactic acid bacteria to the solid substrate fermentation part.

The solid substrate fermentation part may mix the supplied remaining soybean meal and the lactic acid bacteria as a first mixed material, mix the raw soybean meal and the lactic acid bacteria as a second mixed material, or mix the remaining soybean meal, the raw material soybean meal, and the lactic acid bacteria as a third mixed material.

The solid substrate fermentation part may solid substrate ferment one of the first mixed material to the third mixed material and produce primary solid substrate fermented soybean meal.

The drier may include: a fluidized bed drier (for monogastric animals; the remaining soybean meal+the lactic acid bacteria, the remaining soybean meal+the raw material soybean meal+the lactic acid bacteria, and the raw material soybean meal+the lactic acid bacteria), which dries the primary solid substrate fermented soybean meal of the solid substrate fermentation part at a first temperature; and a double mixing drier (for ruminant; the raw material soybean meal+the lactic acid bacteria), which dries the primary solid substrate fermented soybean meal of the solid substrate fermentation part at a second temperature higher than the first temperature.

The double mixing drier may further include a lactic acid bacteria injection nozzle, which is installed to inject a part of the lactic acid bacteria supplied from the lactic acid bacteria service tank to the solid substrate fermentation part into the double mixing drier.

The lactic acid bacteria culturing part may further include a circulating water tank, which supplies circulating water produced by mixing a part of the lactic acid bacteria supplied from the lactic acid bacteria storing tank and the lactic acid bacteria service tank and the soybean meal extract supplied from the solid-liquid separating part to the solid-liquid separating part.

The solid substrate fermentation part may include: a fermentation chamber, which is provided with an inlet, through which the mixed material is introduced, and an outlet, through which the fermented primary solid substrate fermented soybean meal is discharged, to form an insulating space covered by an insulating material, and ferments the mixed material to the primary solid substrate fermented soybean meal; a transfer conveyor, which is installed inside the fermentation chamber and transfers the mixed material and the primary solid substrate fermented soybean meal to the outlet side from the inlet; a blade, which is provided on a shaft, which is installed at the inlet side in a transverse direction of the fermentation chamber and rotates, and sets a height of the mixed material within the fermentation chamber; and a scraper, which is installed on a shaft, which is installed at the outlet side in the transverse direction of the fermentation chamber and forwardly and reversely rotates, with a bracket interposed therebetween, and scraps the primary solid substrate fermented soybean meal fermented in the fermentation chamber and discharges the scraped primary solid substrate fermented soybean meal by each set amount.

The double mixing drier may include: a housing including an inlet, through which the primary solid substrate fermented soybean meal is introduced from the solid substrate fermentation part, and an outlet, through which mixed and dried secondary solid substrate fermented soybean meal is discharged; one pair of rotation shafts, which is elongated in disposition directions of the inlet and the outlet inside the housing and is disposed in parallel at a set interval in a direction crossing the elongation direction; and a plurality of blades, which is slantly installed on the rotation shafts at a set angle, wherein an internal space of the housing may include a fermentation and mixing area, a Maillard reaction area, in which Maillard reaction is generated by the supplied lactic acid bacteria, and a moisture adjusting area by supplied moisture, which are sequentially provided between the inlet and the outlet.

The housing may be provided with an oil jacket, which circulates high-temperature oil, and the rotation shaft and the blades may be provided with oil passages, through which high-temperature oil is circulated.

The grinder may include: a housing, which is provided with an inlet, through which the secondary solid substrate fermented soybean meal is introduced in a lateral direction, and an outlet, through which the ground tertiary solid substrate fermented soybean meal is discharged; rotary blades, which are installed in a plurality of blade mounting portions, which is mounted on a rotation shaft penetrating the housing and is provided at a set rotation interval, respectively; a plurality of stationary blades, which is continuously disposed in a frame disposed in a crushing area in a rotation trace of the rotary blade while maintaining a gap with the rotary blade; and a perforated plate, which is disposed in a discharge area along the remaining area of the crushing area in the rotation trace while maintaining a gap with the rotary blades and discharges the crushed tertiary solid substrate fermented soybean meal to the outlet side.

Advantageous Effects

As described above, in the exemplary embodiment of the present invention, at least two of the remaining soybean meal supplied from the solid-liquid separating part, the raw material soybean meal supplied through bypass, and the lactic acid bacteria supplied from the lactic acid bacteria culturing part are selectively supplied, are mixed and fermented in the solid substrate fermentation part, and are dried in the drier, thereby producing fermented soybean meal for monogastric animals and ruminant selectively or together.

Further, in the exemplary embodiment of the present invention, the lactic acid bacteria culturing part is provided to culture lactic acid bacteria in large numbers with a soybean meal extract, so that it is possible to use the cultured lactic acid bacteria as a starter of fermented soybean meal, and further it is possible to mass produce the remaining lactic acid bacteria used as the starter into probiotics in a liquid state or after drying.

MODE FOR INVENTION

Figure 1:
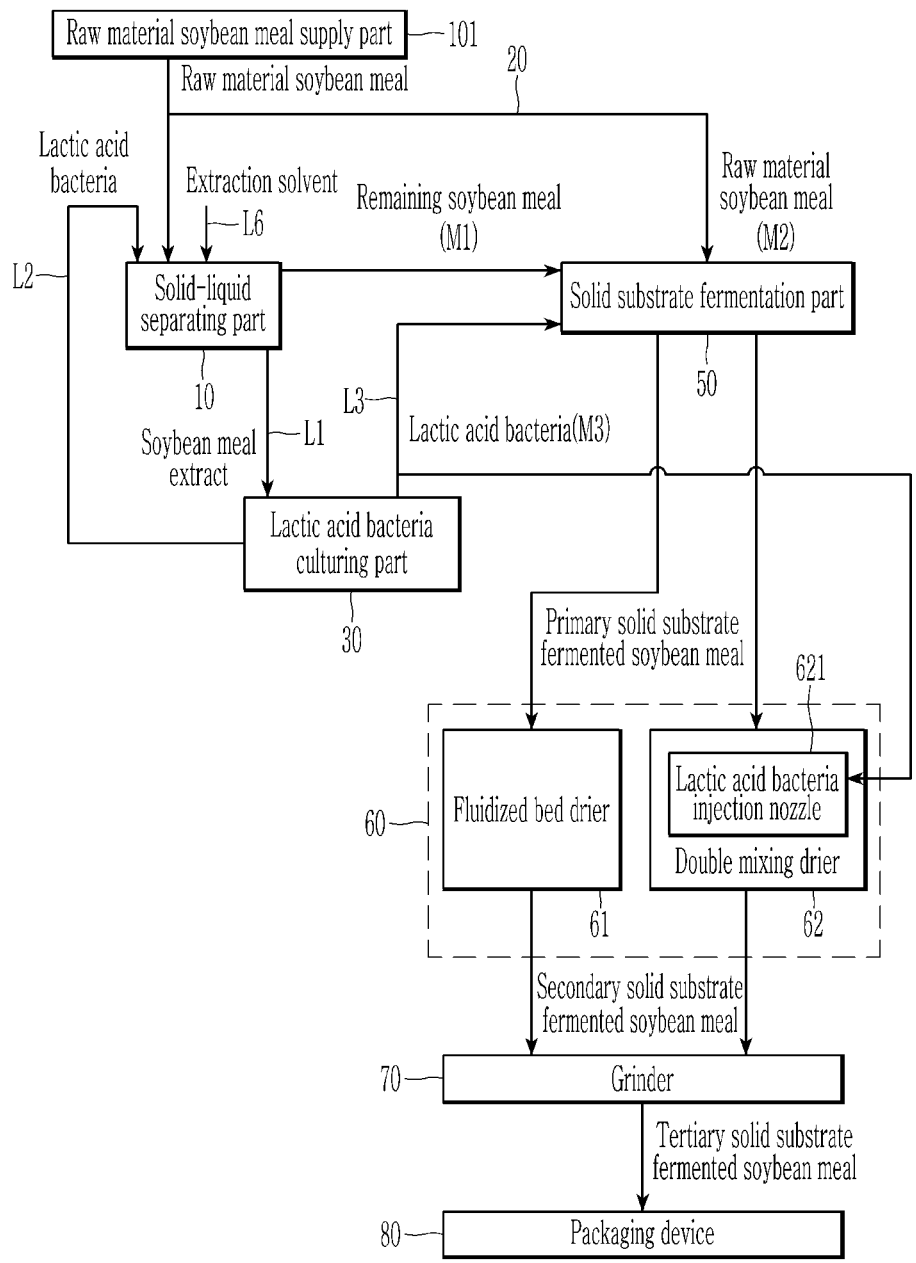
FIG. 1 is a general configuration diagram illustrating an apparatus for producing fermented soybean meal according to an exemplary embodiment of the present invention.

Hereinafter, the present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a general configuration diagram illustrating an apparatus for producing fermented soybean meal according to an exemplary embodiment of the present invention. Referring to FIG. 1, an apparatus for producing fermented soybean meal according to an exemplary embodiment of the present invention includes a solid-liquid separating part 10, a lactic acid bacteria culturing part 30, a solid substrate fermenting part 50, and a drier 60 so as to produce final fermented soybean meal from raw material soybean meal.

Fermented soybean meal for ruminant needs to decompose in the small intestine without decomposing protein in the first rumen, so that the fermented soybean meal for ruminant is called bypass fermented soybean meal. As a principle of producing the bypass fermented soybean meal, Maillard reaction, in which reducing sugar is bonded to lysin at a high temperature, is used.

In the apparatus for producing fermented soybean meal, raw material soybean meal is supplied to the solid-liquid separating part 10 or is supplied while bypassing 20, or is supplied to the solid-liquid separating part 10 and is supplied while bypassing 20 through a raw material soybean meal supplying part 101. For example, the raw material soybean meal supplying part 101 supplies the raw material soybean meal to the solid-liquid separating part 10 or supplies the raw material soybean meal while bypassing 20 the solid-liquid separating part 10. Further, the raw material soybean meal supplying part 101 may bypass 20 the solid-liquid separating part 10 and supply the raw material soybean meal while supplying the raw material soybean meal to the solid-liquid separating part 10 at the same time.

The solid-liquid separating part 10 is configured to mix the raw material soybean meal and an extraction solvent and extract the soybean meal, and separately produce a remaining soybean meal and a soybean meal extract. The soybean meal extract extracted from the extraction solvent and the lactic acid bacteria and the raw material soybean meal is supplied to the lactic acid bacteria culturing part 30 through a first line L1, and the separated remaining soybean meal M1 is supplied to the solid substrate fermenting part 50. The lactic acid bacteria culturing part 30 is configured to produce lactic acid bacteria by putting inoculum into the soybean meal extract, and supply the lactic acid bacteria M3 to the solid-liquid separating part 10 through a second line L2.

The lactic acid bacteria for producing fermented soybean meal is facultative anaerobic bacteria. For example, the facultative anaerobic bacteria may be one or more kinds selected from the group consisting of *Enterococcus faecium*, *Enterococcus faecalis*, *Weissella koreensis*, *Pediococcus pentosaceus*, *Lactobacillus plantarum*, *Lactobacillus lactis*, *Lactobacillus reuteri*, *Lactobacillus brevis*, *Lactobacillus casei*, *Lactobacillus fermentum*, *Lactobacillus bulgaricus*, and *Lactobacillus acidophilus*.

Despite the fact that the solid-liquid separating process progressed in the solid-liquid separating part 10 is an anaerobic fermenting process, in which the predetermined amount of carbohydrate within the raw material soybean meal is removed and lactic acid bacteria is used, the solid-liquid separating process may produce fermented soybean meal having a high content (for example, 53% or more) of crude protein.

After the solid-liquid separating process, the solid substrate fermenting part 50 may adjust a mixing ratio of the remaining soybean meal M1 and the bypassed raw material soybean meal M2, and thus it is possible to produce fermented soybean meal of various contents (for example, 58% or more for fish, 53% or more for piglet and young livestock, and 50% or more for adult animals, such as sow) of crude protein.

The solid substrate fermenting part 50 is selectively supplied with the remaining soybean meal M1 supplied from the solid-liquid separating part 10, the raw material soybean meal M2 supplied while bypassing 20, and the lactic acid bacteria M3 supplied from the lactic acid culturing part 30 through the third line L3, and mixes the remaining soybean meal M1, the raw material soybean meal M2, and the lactic acid bacteria M3.

For example, the solid substrate fermenting part 50 is formed in a double paddle mixer and mixes the remaining soybean meal M1 and the lactic acid bacteria M3, or mixes the remaining soybean meal M1, the raw material soybean meal M2, and the lactic acid bacteria M3 (produces fermented soybean meal for monogastric animals), or mixes the raw material soybean meal M2 and the lactic acid bacteria M3 (produces fermented soybean meal for ruminant)

The solid substrate fermenting part 50 solid-substrate ferments the mixed material to produce the primary solid-substrate fermented soybean meal, which is first processed in a process for producing fermented soybean meal. That is, the mixed material supplied to the solid substrate fermenting part 50 is obtained by mixing the remaining soybean meal M1 and the lactic acid bacteria M3, mixing the remaining soybean meal M1, the raw material soybean meal M2, and the lactic acid bacteria M3, or mixing the raw material soybean meal M2 and the lactic acid bacteria M3, and subsequently solid-substrate fermented to form the primary solid-substrate fermented soybean meal.

The drier 60 dries the primary solid substrate fermented soybean meal supplied from the solid substrate fermenting part 50 and produces the secondary solid substrate fermented soybean meal divided into fermented soybean meal for monogastric animals or ruminant That is, the drier 60 dries the primary solid substrate fermented soybean meal obtained by mixing the remaining soybean meal M1 and the lactic acid bacteria M3, mixing the remaining soybean meal M1, the raw material soybean meal M2, and the lactic acid bacteria M3, or mixing the raw material soybean meal M2 and the lactic acid bacteria M3 at a first temperature (low temperature), and produces fermented soybean meal for monogastric animals (for example, a fluidized bed drier). Further, the drier 60 may dry the primary solid substrate fermented soybean meal obtained by mixing the raw material soybean meal M2 and the lactic acid bacteria M3 at a second temperature (high temperature), and produce fermented soybean meal for ruminant (for example, a double mixing drier).

The apparatus for producing fermented soybean meal of the exemplary embodiment further includes a grinder 70. The grinder 70 grinds the secondary solid substrate fermented soybean meal supplied from the drier 60 and finally produces the tertiary solid substrate fermented soybean meal. The tertiary solid substrate fermented soybean meal is packaged in a packaging device 80.

To describe in detail with reference to FIG. 1, the solid-liquid separating part 10 includes any one of a centrifugal separator, a screw pressor, a filter pressor, and a decanter, which separates the remaining soybean meal and the soybean meal extract from immersion sludge.

The solid-liquid separating part 10 mixes, stirs, and immerses the supplied raw material soybean meal and extraction solvent, supplies and stores the immersion sludge, and separates the remaining soybean meal and the soybean meal extract from the immersion sludge by the centrifugal separator and the like.

For example, the centrifugal separators centrifugally separates the supplied immersion sludge and produces the remaining soybean meal (solid) M1 and the soybean meal extract. The separated remaining soybean meal M1 is supplied to the solid substrate fermenting part 50, and the dehydrated soybean meal extract is supplied to the lactic acid bacteria culturing part 30.

Further, the solid-liquid separating part 10 is supplied with the extraction solvent for extracting a sugar ingredient from the raw material soybean meal through a sixth line L6. The extraction solvent is produced by mixing tap water supplied through a fourth line L4, circulating water which circulates the lactic acid bacteria culturing part 30 and is supplied through a fifth line L5, and a separately supplied acidified material (for example, hydrochloric acid). The acidified material, and the tap water and the circulating water of the fourth and fifth lines L4 and L5 are the examples for producing the extraction solvent, but the configuration of producing the extraction solvent and the ingredients of the extraction solvent are not limited.

Figure 2:
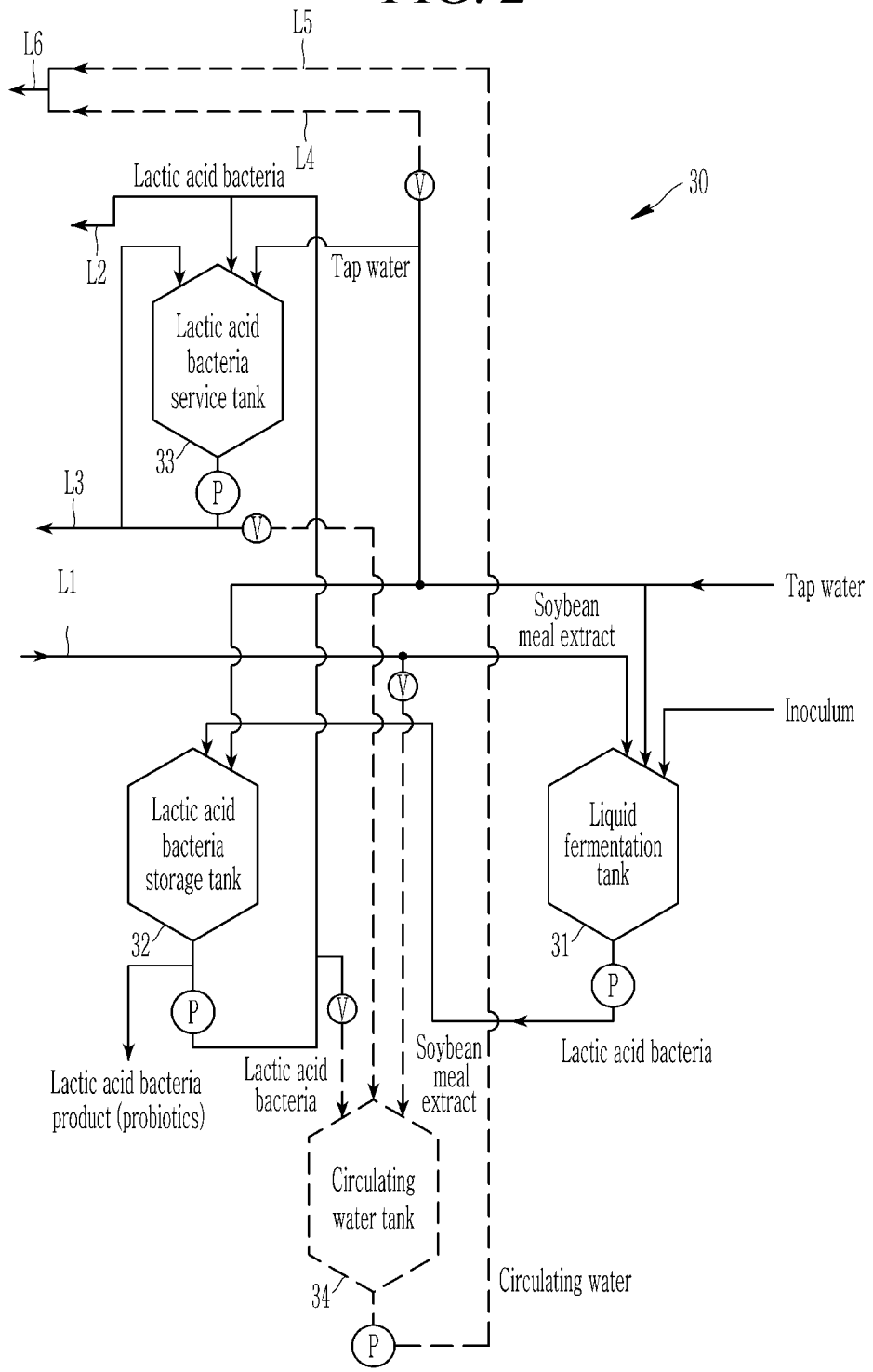
FIG. 2 is a configuration diagram illustrating a lactic acid bacteria culturing part, which produces lactic acid bacteria from a soybean meal extract, in FIG. 1 in more detail.

FIG. 2 is a configuration diagram illustrating the lactic acid bacteria culturing part, which produces lactic acid bacteria from a soybean meal extract, in FIG. 1 in more detail. Referring to FIGS. 1 and 2, the lactic acid bacteria culturing part 30 includes a liquid fermentation tank 31, a lactic acid bacteria storing tank 32, and a lactic acid bacteria service tank 33.

The liquid fermentation tank 31 is connected to the solid-liquid separating part 10, and performs liquid-fermentation by injecting inoculum into the soybean meal extract supplied from the solid-liquid separating part 10 and the tap water separately supplied through the fourth line L4 one time to generate lactic acid bacteria, and supplies the generated lactic acid bacteria to the lactic acid bacteria storing tank 32 through the driving of a pump P provided at an outlet.

The lactic acid bacteria storing tank 32 is connected to the liquid fermentation tank 31 and mixes the lactic acid bacteria supplied from the liquid fermentation tank 31 with the more tap water supplied through the fourth line L4 to mass produce and store lactic acid bacteria, and supplies the lactic acid bacteria to the lactic acid bacteria service tank 33 and the solid-liquid separating part 10 through the driving of the pump P provided at the outlet.

The lactic acid bacteria stored in the lactic acid bacteria storing tank 32 may be separately supplied and used for producing a lactic acid bacteria product (probiotics).

The lactic acid bacteria service tank 33 is connected to the lactic acid bacteria storing tank 32, and temporally stores the lactic acid bacteria supplied from the lactic acid bacteria storing tank 32 and the tap water supplied through the fourth line L4 and supplies the lactic acid bacteria and the tap water to the solid substrate fermenting part 50 through the driving of the pump P provided at the outlet.

The lactic acid bacteria culturing part 30 further includes a circulating water tank 34. The circulating water tank 34 is connected to the lactic acid bacteria storing tank 32 and the lactic acid bacteria service tank 33, and mixes some lactic acid bacteria among the lactic acid bacteria supplied from the lactic acid bacteria storing tank 32 to the lactic acid bacteria service tank 33 and the soybean meal extract supplied from the solid-liquid separating part 10 to produce circulating water, and supplies the circulating water to the solid-liquid separating part 10 connected to the circulating water tank 34 through a fifth line L5 and the sixth line L6 through the driving of the pump P provided at the outlet.

The circulating water is not essential for the process of producing fermented soybean meal, but is reused and is used for washing the producing apparatus including tap water, thereby helping the producing apparatus to be efficiently operated. The circulating water supplied to the solid-liquid separating part 10 through the fifth line L5 is mixed with tap water and hydrochloric acid to form an extraction solvent, and is supplied to the solid-liquid separating part 10 through the sixth line L6.

To this end, valves V are provided at inflow sides from the second and third lines L2 and L3 to the circulating water tank 34, respectively, to interrupt inflow of the lactic acid bacteria, a valve V is provided at an inflow side from the first line L1 to the circulating water tank 34 to interrupt inflow of the soybean meal extract, and a valve V is provided at a discharge side from the circulating water tank 34 to the fifth line L5 to interrupt discharge of the circulating water.

Further, a valve V is provided at an inflow side from the fourth line L4 to the solid-liquid separating part 10 to interrupt inflow of the tap water to the solid-liquid separating part 10. The circulating water tank 34, the solid-liquid separating part 10, the first line L1 to the fifth line L5, and the valves V are exemplified as one exemplary embodiment for producing the extraction solvent, but the ingredients of the extraction solvent and the configuration for producing the extraction solvent are not limited.

Although not particularly illustrated, valves for a required control may be further included in the first line to the sixth line and inlet and outlet sides of the various tanks.

Referring back to FIG. 1, the solid substrate fermenting part 50 mixes the remaining soybean meal M1 and the lactic acid bacteria M3, which are supplied according to a produced product of the fermented soybean meal, as a first mixed material, mixes the raw material soybean meal M2 and the lactic acid bacteria M3 as a second mixed material, and mixes the remaining soybean meal M1, the raw material soybean meal M2, and the lactic acid bacteria M3 as a third mixed material.

The solid substrate fermenting part 50 solid-substrate ferments the mixed first mixed material (M1+M3), second mixed material (M2+M3), and third mixed material (M1+M2+M3) to produce primary solid substrate fermented soybean meal. That is, the primary solid substrate fermented soybean meal is produced by the first mixed material (M1+M3), the second mixed material (M2+M3), or the third mixed material (M1+M2+M3).

The drier 60 includes a fluidized bed drier 61 and a double mixing drier 62, which are selectively used according to the first mixed material (M1+M3), the second mixed material (M2+M3), or the third mixed material (M1+M2+M3) supplied, the drying at the first temperature (low temperature) or the drying at the second temperature (high temperature), and the monogastric animal or the ruminant That is, the solid-liquid separating part 10, the bypass 20, and the lactic acid bacteria culturing part 30 may produce the fermented soybean meal for the monogastric animal or the ruminant according to the first, second, and third mixed materials (M1+M3, M2+M3, and M1+M2+M3), and the fluidized bed drier 61 and the double mixing drier 62.

The fluidized bed drier 61 dries the primary solid substrate fermented soybean meal supplied from the solid substrate fermenting part 50 at a low temperature to produce secondary solid substrate fermented soybean meal. In this case, the supplied primary solid substrate fermented soybean meal may be the first mixed material (M1+M3) and the third mixed material (M1+M2+M3) dried at the low temperature for the monogastric animal or the second mixed material (M2+M3) dried at the low temperature for the ruminant For example, the fluidized bed drier 61 dries the supplied primary solid substrate fermented soybean meal at the first temperature (for example, 50 to 80° C.). The fluidized bed drier 61 is configured in a continuous type, and mainly dries the primary solid substrate soybean meal as the first mixed material (M1+M3) and the third mixed material (M1+M2+M3) for the monogastric animal while minimizing thermal denaturalization of the primary solid substrate fermented soybean meal passing through the solid-liquid separating part 10.

The double mixing drier 62 dries the primary solid substrate fermented soybean meal at the second temperature (high temperature), which is higher than the first temperature (low temperature) of the fluidized bed drier 61, and dries the primary solid substrate fermented soybean meal supplied from the solid substrate fermenting part 50 at the second temperature (high temperature) to produce secondary solid substrate fermented soybean meal. In this case, the supplied primary solid substrate fermented soybean meal is the second mixed material (M2+M3) dried at the second temperature (high temperature) for ruminant The double mixing drier 62 mainly dries the primary solid substrate fermented soybean meal as the second mixed material (M2+M3) for the ruminant The double mixing drier 62 dries the primary solid substrate fermented soybean meal passing through the bypass 20 as the second mixed material (M2+M3) for the ruminant For example, the double mixing drier 62 maintains the second temperature (for example, 100 to 150° C.) higher than that of the fluidized bed drier 61 (Maillard reaction). Reducing sugar amino acid (lysine) is highly bonded at the second temperature (high temperature).

The double mixing drier 62 further includes a lactic acid bacteria injection nozzle 621 installed therein. The lactic acid bacteria injection nozzle 621 injects a part of the lactic acid bacteria which are supplied from the lactic acid bacteria service tank 33 to the solid substrate fermenting part 50 into the double mixing drier 62. The lactic acid bacteria injection nozzle 621 injects lactic acid bacteria to the primary solid substrate fermented soybean meal which is dried at the high temperature to make the Millard reaction be uniform.

Figure 3:
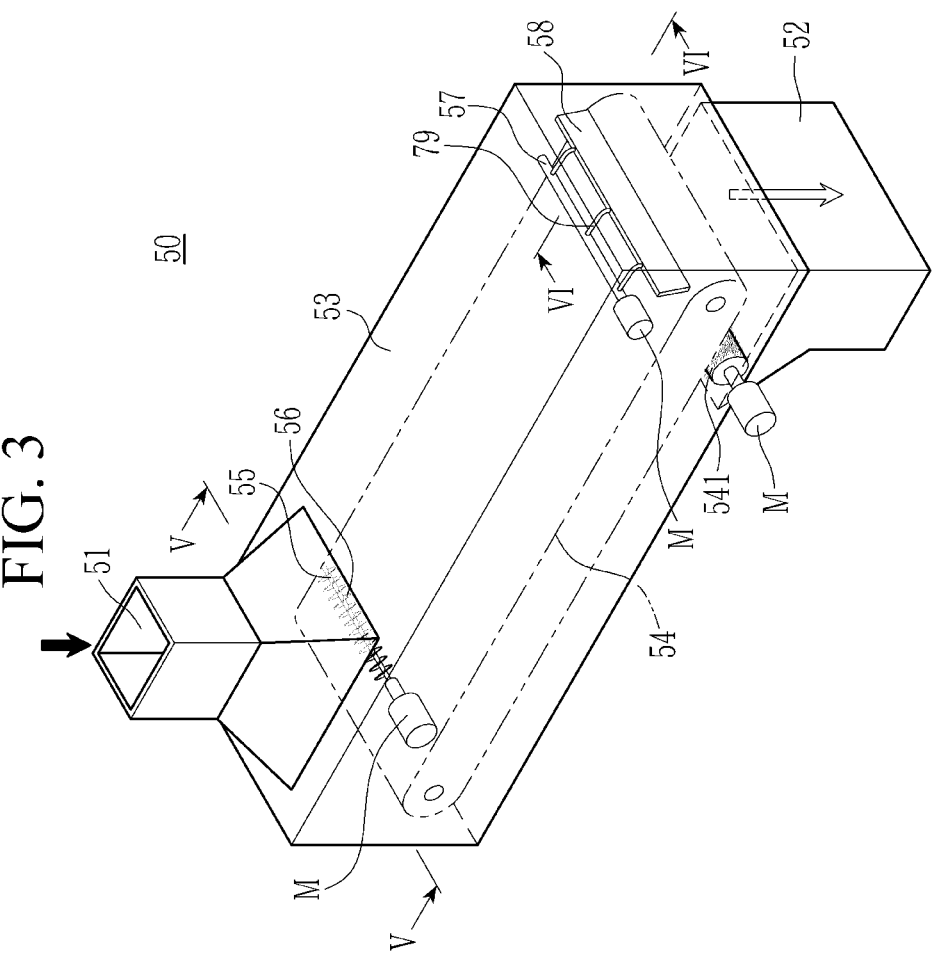
FIG. 3 is a perspective view illustrating a solid substrate fermenting part of FIG. 1.
Figure 4:
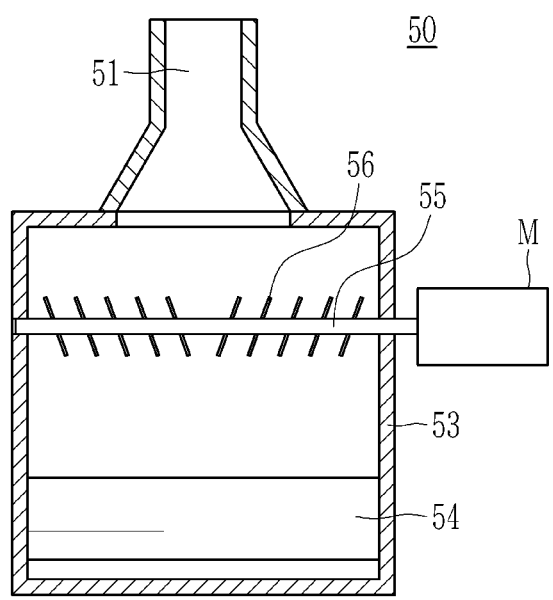
FIG. 4 is a cross-sectional view taken along line V-V of FIG. 3.
Figure 5:
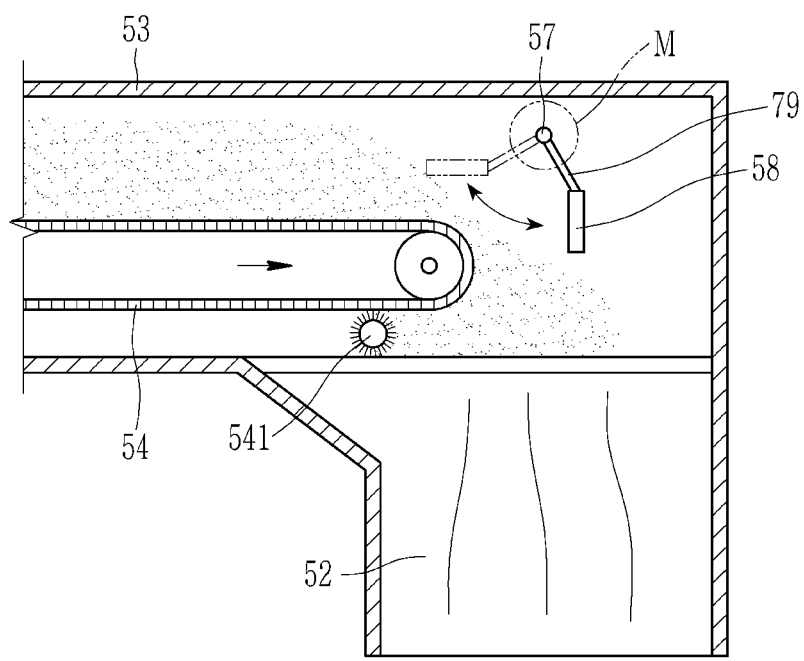
FIG. 5 is a cross-sectional view taken along line VI-VI of FIG. 3.

FIG. 3 is a perspective view illustrating the solid substrate fermenting part of FIG. 1, FIG. 4 is a cross-sectional view taken along line V-V of FIG. 3, and FIG. 5 is a cross-sectional view taken along line VI-VI of FIG. 3.

Referring to FIGS. 3 to 5, the solid substrate fermenting part 50 includes a fermentation chamber 53 including an inlet 51 and an outlet 52, a transfer conveyer 54, a shaft 55, a blade 56, a shaft 57, and a scraper 58.

The inlet 51 makes the first, second, and third mixed materials (M1+M3, M2+M3, and M1+M2+M3), which are mixed and supplied, flow into the fermentation chamber 53, and the outlet 52 discharges the primary solid substrate fermented soybean meal which is fermented inside the fermentation chamber 53. The fermentation chamber 53 is formed with an insulating space covered by an insulating material.

The transfer conveyor 54 is installed at the side of the inlet 61 in the direction of the outlet 52 inside the fermentation chamber 53 to transfer the first, second, and third mixed materials M1+M3, M2+M3, and M1+M2+M3) supplied to the inlet 51 and the fermented primary solid substrate fermented soybean meal to the side of the outlet 52 (for example, 0.9 m/h).

The shaft 55 is installed at the side of the inlet 51 in a transverse direction of the fermentation chamber 53 to rotate by the driving of a motor M. The blade 56 is spirally provided on the shaft 55 and sets heights (for example, 1.3 m) of the first, second, and third mixed materials M1+M3, M2+M3, and M1+M2+M3) stacked inside the fermentation chamber 53 at the side of the inlet 51 to be appropriate for the solid substrate fermentation while rotating according to the rotation of the shaft 55.

The shaft 57 is installed at the side of outlet 52 in the transverse direction of the fermentation chamber 53 to forwardly and reversely rotate by the driving of a forward/reverse rotary motor M. Although not illustrated, the motor may be switched to a hydraulic cylinder and a configuration of operating the shaft with the hydraulic cylinder may also be added. The scraper 58 is installed in the shaft 57 with a bracket 79 interposed therebetween, and scrapes the primary solid substrate fermented soybean meal fermented in the fermentation chamber 53 and discharges the scraped primary solid substrate fermented soybean meal to the outlet 52 by each set amount while repeatedly rotating forwardly and reversely according to the driving of the motor M.

For example, the solid substrate fermenting part 50 forms a continuous fermentation part by the transfer conveyor 54, and implements the fermentation without the additional supply of air for about 24 hours, and a fermented product is maintained with moisture of 35 to 65% at a fermentation temperature of 25 to 45° C.

When the first, second, and third mixed materials (M1+M3, M2+M3, and M1+M2+M3) are inserted into the inlet 51, the first, second, and third mixed materials (M1+M3, M2+M3, and M1+M2+M3) maintain the predetermined heights within the fermentation chamber 53 by the shaft 55 and the blade 56, and the primary solid substrate fermented soybean meal fermented within the fermentation chamber 53 is discharged by a predetermined amount by the shaft 57, the bracket 79, and the scraper 58.

As described above, the shaft 55 and the blade 56 stack the inflow first, second, and third mixed materials (M1+M3, M2+M3, and M1+M2+M3) with the set height at the inlet 51, and the shaft 57 and the scraper 58 discharge the fermented primary solid substrate fermented soybean meal by the predetermined amount at the outlet 52, so that the primary solid substrate fermented soybean meal may be stably solid substrate fermented in the solid substrate fermenting part 50.

Further, a brush 541 provided at a lower side of the transfer conveyor 54 in a width direction brushes the primary solid substrate fermented soybean meal attached to the return side of the transfer conveyor 54 and discharges the primary solid substrate fermented soybean meal to the outlet 52 while being driven by the motor M provided on a shaft of the brush 541 and rotating.

Figure 6:
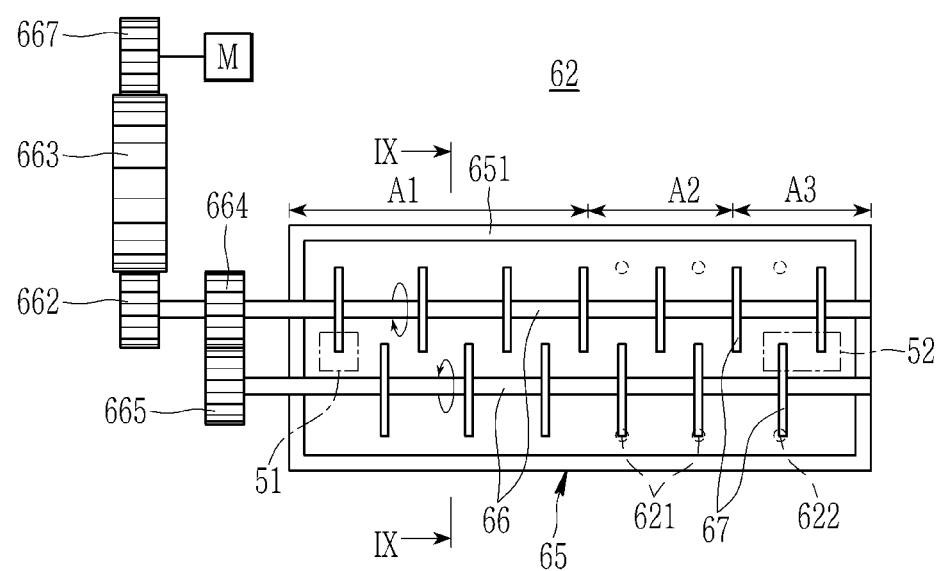
FIG. 6 is a schematic plane view of a double mixing drier implementing high-temperature drying in FIG. 1.
Figure 7:
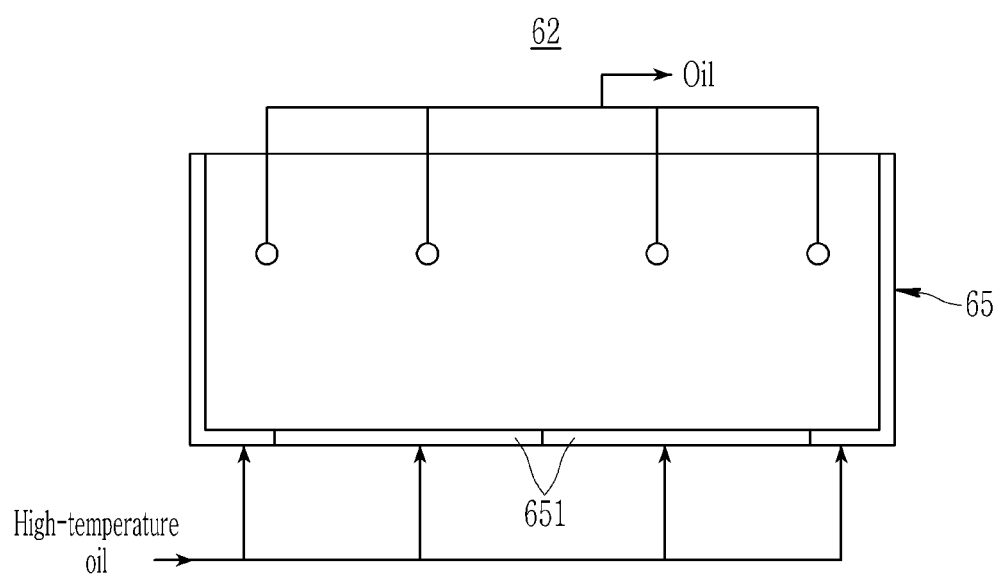
FIG. 7 is a schematic lateral view of the double mixing drier of FIG. 6.
Figure 8:
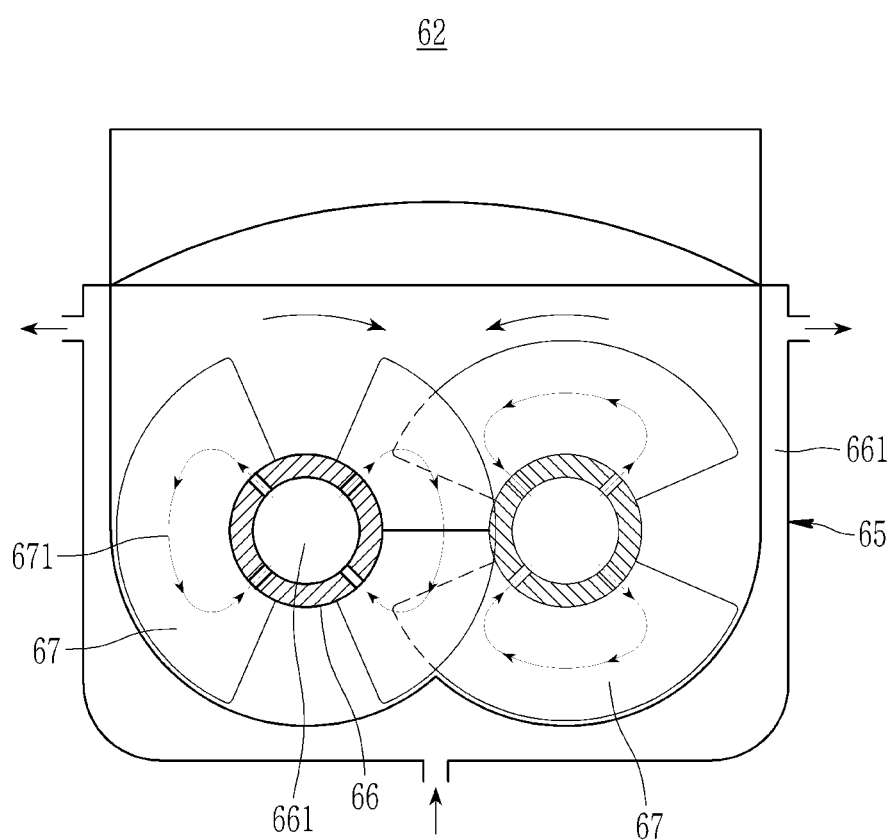
FIG. 8 is a schematic cross-sectional view taken along line IX-IX of FIG. 6.

FIG. 6 is a schematic plane view of the double mixing drier implementing high-temperature drying in FIG. 1, FIG. 7 is a schematic lateral view of the double mixing drier of FIG. 6, and FIG. 8 is a schematic cross-sectional view taken along line IX-IX of FIG. 6.

Referring to FIGS. 6 to 8, the double mixing drier 62 includes a housing 65 including an inlet 63 and an outlet 64, one pair of rotation shafts 66, and blades 67 in order to produce the secondary solid substrate fermented soybean meal by mixing the inflow primary solid substrate fermented soybean meal and drying the primary solid substrate fermented soybean meal at a high temperature.

The inlet 63 allows the primary solid substrate fermented soybean meal to flow in from the solid substrate fermenting part 50, the housing 65 produces the secondary solid substrate fermented soybean meal by mixing the inflow primary solid substrate fermented soybean meal and drying the primary solid substrate fermented soybean meal at a high temperature, and the outlet 64 allows the produced secondary solid substrate fermented soybean meal to be discharged.

The one pair of rotation shafts 66 and the blades 67 enable the secondary solid substrate fermented soybean meal, which is produced from the inflow primary solid substrate fermented soybean meal, to be smoothly discharged. That is, the one pair of rotation shafts 66 is elongated in a disposition direction (the left and right directions in FIG. 6) of the inlet 63 and the outlet 64 inside the housing 65, and are disposed in parallel at a set interval in a direction (the upper and lower directions in FIG. 6) crossing the rotation shafts 66.

The one pair of rotation shafts 66 connects a driving sprocket 667 and a driven sprocket 662 through a chain 663, and is connected to rotate by driving the driving sprocket 667 with the motor M. The one pair of rotation shafts 66 includes first and second gears 664 and 665, which are gear-engaged with each other at an external side of the housing 65, and one rotation shaft 66 in the one pair of rotation shafts is connected to the driven sprocket 662.

Accordingly, one rotation shaft 66 is driven through the transmission of power to the driving sprocket 667, the chain 663, and the driven sprocket 662 by the driving of the motor M, and the other rotation shaft 66 is also driven by the first and second gears 664 and 665.

The blades 67 are staggered and disposed so as to alternate with each other in the one pair of rotation shafts 66, and are slantly installed at a set angle. Accordingly, the blades 67 provided in the one pair of rotation shafts 66 move the secondary solid substrate fermented soybean meal, which is produced by mixing and drying the primary solid substrate fermented soybean meal while rotating in opposite directions, to the outlet 64 side.

An internal space of the housing 65 includes a fermentation mixing area A1, a Maillard reaction area A2, in which the Maillard reaction is generated by the supplied lactic acid bacteria, and a moisture adjusting area A3 by the supplied moisture, which are sequentially provided between the inlet 63 and the outlet 64.

To this end, the lactic acid bacteria injection nozzle 621 is provided in the Maillard reaction area A2 and injects the lactic acid bacteria to the primary fermented soybean meal, which is being mixed and dried, so that the Millard reaction is uniformly generated in the Maillard reaction area A2.

A water injection nozzle 662 is provided in the moisture adjusting area A3, and injects water or the lactic acid bacteria to the primary fermented soybean meal, which is being mixed, dried, and is under the Millard reaction, so that the moisture of the primary solid substrate fermented soybean meal is adjusted in the moisture adjusting area A3.

In the double mixing drier 62, which produces the secondary solid substrate fermented soybean meal with the primary solid substrate fermented soybean meal through the mixing, the drying, the Millard reaction, and the moisture adjustment, the housing 65 includes an oil jacket 651, which circulates high-temperature oil, and the rotation shaft 66 and the blades 67 are provided with oil passages 661 and 671, through which the high-temperature oil circulates. The oil jacket 651 and the oil passages 661 and 671 enable the high-temperature drying to be performed in the double mixing drier 62.

Figure 9:
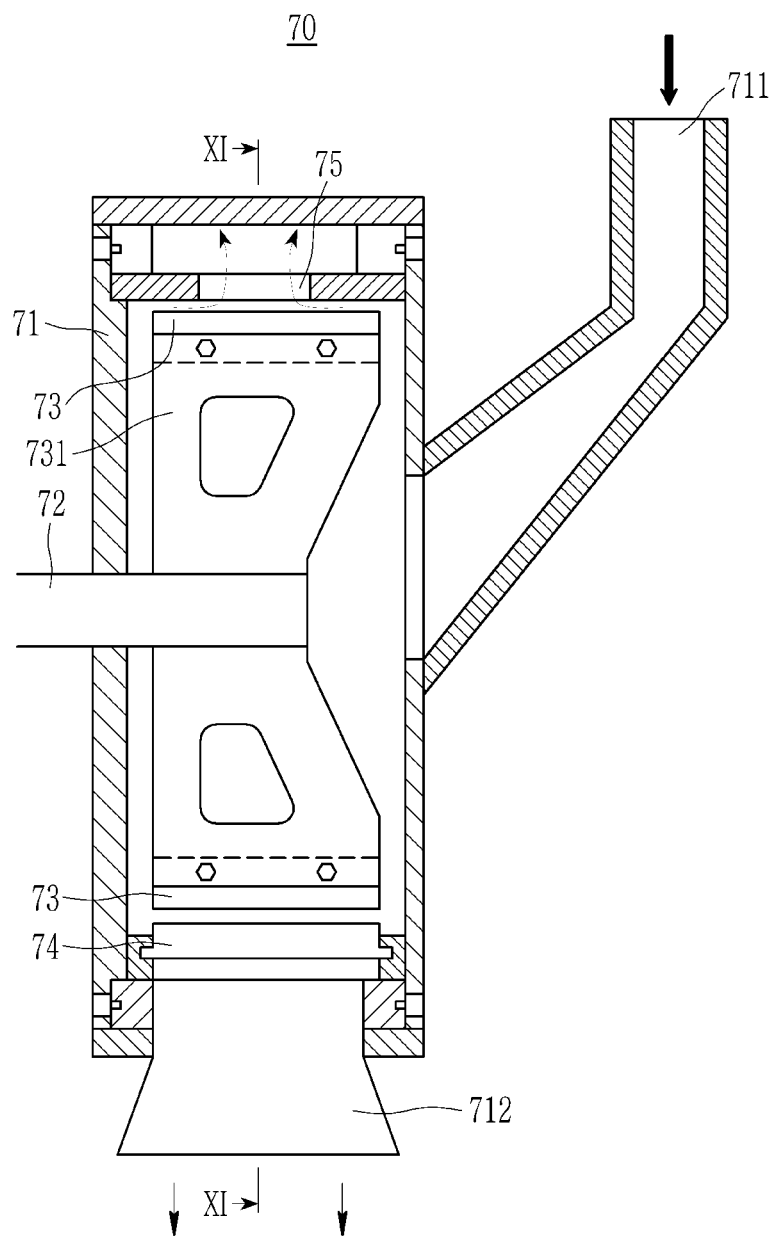
FIG. 9 is a cross-sectional view illustrating a grinder of FIG. 1.
Figure 10:
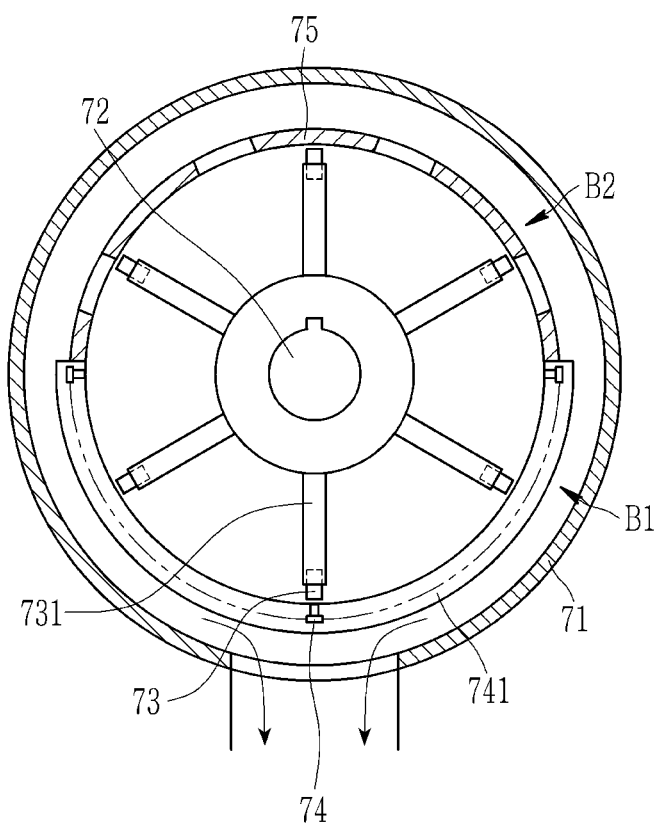
FIG. 10 is a schematic cross-sectional view taken along line XI-XI of FIG. 9.
Figure 11:
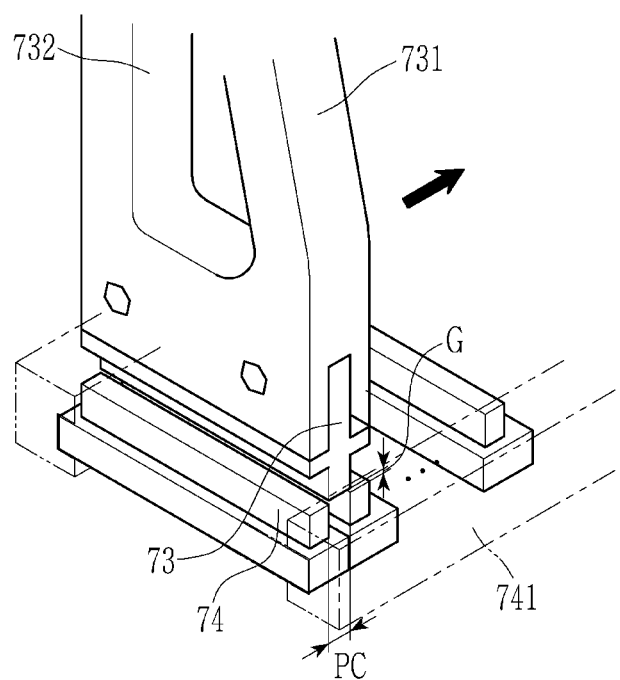
FIG. 11 is a partial perspective view illustrating the case where fermented soybean meal is ground by a stationary blade and a rotary blade in FIGS. 9 and 10 in detail.

FIG. 9 is a cross-sectional view illustrating the grinder of FIG. 1, FIG. 10 is a schematic cross-sectional view taken along line XI-XI of FIG. 9, and FIG. 11 is a partial perspective view illustrating the case where fermented soybean meal is ground by a stationary blade and a rotary blade in FIGS. 9 and 10 in detail.

Referring to FIGS. 9 to 11, the grinder 70 includes a housing 71, a rotation shaft 72, a blade mounting portion 731, a rotary blade 73, a frame 741, stationary blades 74, and a perforated plate 75 in order to grind the secondary solid substrate fermented soybean meal to tertiary solid substrate fermented soybean meal that is powder of 35 mesh or less.

The housing 71 includes an inlet 711, through which the secondary solid substrate fermented soybean meal is introduced in a lateral direction (the right side in FIG. 9), and an outlet 712, through which the ground tertiary solid substrate fermented soybean meal is discharged in the lower direction.

The rotation shaft 72 is installed while penetrating the housing 71, the plurality of blade mounting portions 731 is provided in the rotation shaft 72 at a set rotation interval, and the rotary blades 73 are installed in the plurality of blade mounting portions 731, respectively. The blade mounting portions 731 are formed with through-openings 732, thereby effectively discharging heat generated during the grinding.

The frame 741 is disposed in a crushing area B1 according to rotation traces of the rotary blades 73. The plurality of stationary blades 74 is continuously disposed in the frame 741 according to the rotation trace while maintaining gaps G with the rotary blades 73.

The rotary blades 73 and the stationary blades 74 have lengths in a width direction (the left and right directions in FIG. 9) of the housing 71, and perform mutual shearing to perform crushing. Further, the stationary blades 74 are installed in the frame 741, and have pitches PC set toward the rotary blades 73. Accordingly, when the rotary blades 73 and the stationary blades 74 grind the secondary solid substrate fermented soybean meal to the tertiary solid substrate fermented soybean meal, heat is little generated, thereby minimizing thermal denaturalization of the tertiary solid substrate fermented soybean meal.

The perforated plate 75 is disposed in a discharge area B2 along the remaining area of the crushing area B1 in the rotation trace while maintaining a gap with the rotary blades 73 to discharge the crushed tertiary solid substrate fermented soybean meal to the side of the outlet 712.

Referring back to FIG. 1, the tertiary solid substrate fermented soybean meal passing through the grinder 70 passes through a cooler (not illustrated) and a selector (not illustrated), and is supplied to the packaging device 80 and is packaged. The cooler reduces a temperature of the produced tertiary solid substrate fermented soybean meal, which passes through the drier 60 and is before ground or packaged. The selector may be formed with a vibrating screen and select and package a product of 35 mesh or less.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

| <Description of symbols> | |
|---|---|
| 10: Solid-liquid separating part | 20: Bypass |
| 30: Lactic acid bacteria culturing part | 31: Liquid fermentation tank |
| 32: Lactic acid bacteria storing tank | |
| 33: Lactic acid bacteria service tank | |
| 34: Circulating water tank | 44: Lactic acid bacteria service tank |
| 50: Solid substrate fermenting part | 51: Inlet |
| 52: Outlet | 53: Fermentation chamber |
| 54: Transfer conveyor | 55, 57: Shaft |
| 56: Blade | 58: Scraper |
| 60: Drier | 61: Fluidized bed drier |
| 62: Double mixing drier | 63: Inlet |
| 64: Outlet | 65: Housing |
| 66: Rotation shaft | 67: Blades |
| 70: Grinder | 71: Housing |
| 72: Rotation shaft | 73: Rotary blade |
| 74: Stationary blade | 75: Perforated plate |
| 79: Bracket | 80: Packaging device |
| 101: Raw material soybean meal supplying part | |
| 541: Brush | |
| 621: Lactic acid bacteria injection nozzle | |
| 622: Water injection nozzle | |
| 651: Oil jacket | 661, 671: Oil passage |
| 662: Driven sprocket | 663: Chain |
| 664: First gear | 665: Second gear |
| 667: Driving sprocket | 711: Inlet |
| 712: Outlet | 731: Blade mounting portion |
| 732: Through-openings | 741: Frame |
| A1: Fermentation mixing area | A2: Maillard reaction area |
| A3: Moisture adjusting area | B1: Crushing area |
| B2: Discharge area | G: Gap |
| L1, L2, L3: First, second, third line | |
| L4, L5, L6: Fourth, fifth, sixth lines | |
| M: Motor | M1: Remaining soybean meal |
| M1 + M3: First mixed material | M1 + M2 + M3: Third mixed material |
| M2: Raw material soybean meal | M2 + M3: Second mixed material |
| M3: Lactic acid bacteria | P: Pump |
| PC: Pitch | V: Valve |

The invention claimed is:

1. An apparatus for producing fermented soybean meal, the apparatus comprising:
a solid-liquid separating part, which mixes raw material soybean meal and an extraction solvent and extracts soybean meal, and separately produces a remaining soybean meal and a soybean meal extract;
a lactic acid bacteria culturing part, which produces lactic acid bacteria by putting inoculum into the soybean meal extract, and supplies the lactic acid bacteria to the solid-liquid separating part;
a solid substrate fermentation part, which is selectively supplied with and mixes at least two of the remaining soybean meal supplied from the solid-liquid separating part, the raw material soybean meal supplied through a bypass, and lactic acid bacteria supplied from the lactic acid bacteria culturing part to produce a mixed material, and solid-substrate ferments the mixed material to produce primary solid substrate fermented soybean meal; and
a drier, which dries the primary solid substrate fermented soybean meal supplied from the solid substrate fermentation part to produce secondary solid substrate fermented soybean meal,
wherein the solid substrate fermentation part includes:
a fermentation chamber, which is provided with an inlet, through which the mixed material is introduced, and an outlet, through which the fermented primary solid substrate fermented soybean meal is discharged, and ferments the mixed material to the primary solid substrate fermented soybean meal;
a transfer conveyor, which is installed inside the fermentation chamber and transfers the mixed material and the primary solid substrate fermented soybean meal to an outlet side from the inlet; and
a brush, which is provided at a lower side of the transfer conveyor in a width direction and brushes the primary solid substrate fermented soybean meal attached to the return side of the transfer conveyor,
wherein the drier comprises:
a fluidized bed drier, which dries the primary solid substrate fermented soybean meal of the solid substrate fermentation part at a first temperature; and
a double mixing drier, which dries the primary solid substrate fermented soybean meal of the solid substrate fermentation part at a second temperature higher than the first temperature.

2. The apparatus of claim 1, further comprising:
a grinder, which grinds the secondary solid substrate fermented soybean meal supplied from the drier and finally produces tertiary solid substrate fermented soybean meal.

3. The apparatus of claim 2, wherein:
the grinder includes:
a housing, which is provided with an inlet, through which the secondary solid substrate fermented soybean meal is introduced in a lateral direction, and an outlet, through which a ground tertiary solid substrate fermented soybean meal is discharged;
rotary blades, which are installed in a plurality of blade mounting portions, which are mounted on a rotation shaft penetrating the housing and is provided at a set rotation interval, respectively;
a plurality of stationary blades, which are continuously disposed in a frame disposed in a crushing area in a rotation trace of the rotary blades while maintaining a gap with the rotary blades; and
a perforated plate, which is disposed in a discharge area along a remaining area of the crushing area in the rotation trace while maintaining a gap with the rotary blades and discharges a crushed tertiary solid substrate fermented soybean meal to an outlet side.

4. The apparatus of claim 1, wherein:
the solid-liquid separating part is configured to
mix supplied raw material soybean meal and an extraction solvent and immerses the soybean meal,
separate the remaining soybean meal and the soybean meal extract from an immersed immersion sludge,
supply the separated remaining soybean meal to the solid substrate fermentation part, and
supply the dehydrated soybean meal extract to the lactic acid bacteria culturing part.

5. The apparatus of claim 4, wherein:
the solid-liquid separating part includes
any one of a centrifugal separator, a screw pressor, a filter pressor, and a decanter, which separates the remaining soybean meal and the soybean meal extract from the immersion sludge.

6. The apparatus of claim 1, wherein:

the solid-liquid separating part mixes supplied tap water, circulating water, which circulates the lactic acid bacteria culturing part, and acidified material to produce the extraction solvent.

7. The apparatus of claim 1, wherein:

the lactic acid bacteria culturing part includes:

a liquid fermentation tank, which injects the inoculum to the soybean meal extract supplied from the solid-liquid separating part and tap water to produce the lactic acid bacteria;

a lactic acid bacteria storing tank, which is connected to the liquid fermentation tank, and mixes supplied lactic acid bacteria with tap water and stores the lactic acid bacteria; and a lactic acid bacteria service tank, which is connected to the lactic acid bacteria storing tank and supplies the supplied lactic acid bacteria to the solid substrate fermentation part.

8. The apparatus of claim 7, wherein:

the solid substrate fermentation part mixes supplied remaining soybean meal and the lactic acid bacteria as a first mixed material, mixes the raw material soybean meal and the lactic acid bacteria as a second mixed material, or mixes the remaining soybean meal, the raw material soybean meal, the lactic acid bacteria as a third mixed material.

9. The apparatus of claim 8, wherein:

the solid substrate fermentation part solid-substrate ferments one of the first mixed material to the third mixed material and produces the primary solid substrate fermented soybean meal.

10. The apparatus of claim 7, wherein:

the lactic acid bacteria culturing part further includes a circulating water tank, which supplies circulating water produced by mixing a part of the lactic acid bacteria supplied from the lactic acid bacteria storing tank and the lactic acid bacteria service tank and the soybean meal extract supplied from the solid-liquid separating part to the solid-liquid separating part.

11. The apparatus of claim 1, wherein:

the double mixing drier further includes:

a lactic acid bacteria injection nozzle, which is installed to inject a part of the lactic acid bacteria supplied from the lactic acid bacteria service tank to the solid substrate fermentation part into the double mixing drier.

12. The apparatus of claim 1, wherein:

the solid substrate fermentation part further includes:

a blade, which is provided on a shaft, which is installed at an inlet side in a transverse direction of the fermentation chamber and rotates, and sets a height of the mixed material within the fermentation chamber; and a scraper, which is installed on a shaft, which is installed at the outlet side in the transverse direction of the fermentation chamber and forwardly and reversely rotates, with a bracket interposed therebetween, and scrapes the primary solid substrate fermented soybean meal fermented in the fermentation chamber and discharges the scraped primary solid substrate fermented soybean meal in a set amount.

13. The apparatus of claim 1, wherein:

the double mixing drier includes:

a housing including an inlet, through which the primary solid substrate fermented soybean meal is introduced from the solid substrate fermentation part, and an outlet, through which mixed and dried secondary solid substrate fermented soybean meal is discharged;

one pair of rotation shafts, which are elongated in disposition in a direction of the inlet and the outlet inside the housing and is disposed in parallel at a set interval in a direction crossing the elongation direction; and a plurality of blades, which are slantly installed on the pair of rotation shafts at a set angle, and wherein an internal space of the housing includes a fermentation and mixing area, a Maillard reaction area, in which a Maillard reaction is generated by supplied lactic acid bacteria, and a moisture adjusting area by supplied moisture, which are sequentially provided between the inlet and the outlet.

14. The apparatus of claim 13, wherein:

the housing is provided with an oil jacket, which circulates high-temperature oil, and the rotation shafts and the plurality of blades are provided with oil passages, through which the high-temperature oil is circulated.

* * * * *